United States Patent [19]

Chang

[11] Patent Number: 4,868,310

[45] Date of Patent: Sep. 19, 1989

[54] PROCESS FOR PREPARING ISOTHIAZOLONES

[75] Inventor: Sou-Jen Chang, Horsham, Pa.

[73] Assignee: Rohm and Haas Company, Philadelphia, Pa.

[21] Appl. No.: 892,961

[22] Filed: Aug. 4, 1986

[51] Int. Cl.$^4$ .................. C07D 275/02; C07C 102/08; C07C 149/06; C07C 149/14

[52] U.S. Cl. .................................... 548/213; 564/131; 564/162; 564/192; 564/204; 564/207; 564/161

[58] Field of Search ................ 548/213; 564/131, 192, 564/204, 162, 207, 161

[56] References Cited

U.S. PATENT DOCUMENTS

| | | | |
|---|---|---|---|
| 3,022,344 | 2/1962 | Heininger et al. | 564/162 |
| 3,029,279 | 4/1962 | Kondo | 562/556 |
| 3,151,157 | 9/1964 | Fugate et al. | 564/131 |
| 3,840,586 | 10/1974 | Chiba et al. | 560/147 |
| 3,849,430 | 11/1974 | Lewis et al. | 548/213 |
| 4,052,440 | 10/1977 | Gladstone et al. | 560/147 |
| 4,105,431 | 8/1978 | Lewis et al. | 71/67 |

FOREIGN PATENT DOCUMENTS 55998047 6/1984 Japan .
2103216 2/1983 United Kingdom .

OTHER PUBLICATIONS

Bauer et al., *J. Org. Chem.*, 26, p. 1443 (1961).
Glikmans et al., *Bull. Soc. Chim. France*, p. 1376 (1966).
Krimen et al., *Organic Reactions*, 17, pp. 261 and 271, (1969).
"Handbook of Chemistry and Physics", (53rd Ed.), R. C. Weast (Editor), p. C-190 (1973).
Zh. Org. Khim., 5, 1938 (1969), "Kinetics of the Addition of Thiourea to Acrylic Acid".
Abstract for Japan Patent 59/98047 (6/6/84).

*Primary Examiner*—Donald G. Daus
*Assistant Examiner*—E. Bernhardt
*Attorney, Agent, or Firm*—Terence P. Strobaugh

[57] ABSTRACT

The process involves the cofeeding of an acrylonitrile with an appropriate alcohol or its equivalent and a strong acid to form an acrylamide which is thiolated to form a mercapto-propionamide which is halogenated to afford the desired biocidally active isothiazolones. This invention relates to a novel process for preparing N-substituted 3-mercaptopropionamides, an intermediate in the preparation of isothiazolones.

5 Claims, No Drawings

PROCESS FOR PREPARING ISOTHIAZOLONES

Procedures are already known on how to prepare N-substituted 3-mercaptopropionamides. One procedure involving two steps is Bauer, Ludmig and Welsh, Thomas L., *Addition of Thiourea to Acrylonitriles and Acrylamides*, J. Org. Chem 26, p. 1443, 1444, 1445.

This invention, while still proceeding in two steps, is carried out in a single pot. The first step of the instant invention involves treating an acrylonitrile with an alcohol (or its equivalent) and a strong inorganic acid optionally a solvent may also be employed. When solvents are employed, they may be selected from inert or substantially inert organic solvents including halobenzenes, glacial acetic acid or primary alcohols. The mole ratio of nitrile to alcohol is in the range of from about 0.8 to about 1.2 and the mole ratio of strong inorganic acid to unsaturated nitrile is in the range of from about 1.5 to about 3.0. The reaction is conducted at a temperature in the range of from above the freezing point of the reaction mixture to below the boiling point of the lowest boiling component for a period of time of from about 1 to about 24 hours to yield a compound of the formula:

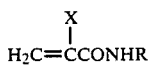

$$H_2C=CCONHR \quad \text{I}$$

wherein R is an unsubstituted or substituted secondary or tertiary alkyl or aralkyl and X is hydrogen, alkyl, such as $C_1$–$C_5$ alkyl and the like, alkenyl such as $C_2$–$C_6$ alkenyl and the like, or aryl such as phenyl, phenylalkyl and the like. The second step of the invention comprising treating the acrylamide (I, supra) with a thiolating agent in the presence of a substantially inert organic solvent and an acid catalyst for from about 0.5 to about 3 hours at a temperature in the range of from about 0° to about 70° C. wherein the mole ratio of the thiolating agent to acrylamide is in the range of from about 0.9 to about 1.2 followed by treating the reaction mixture with a neutralizing amount of strong or weak base at a temperature in the range of from about 0° to about 70° C. for from about 0.5 to about 3 hours to afford N-substituted 3-mercaptopropionamide (II, infra) of the formula:

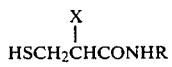

$$HSCH_2CHCONHR \quad \text{II}$$

mwherein X and R are as defined above, which may be isolated or halogenated to afford the desired biocidally active isothiazolone of the formula:

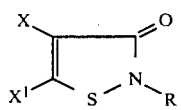

wherein X and R are as defined above and $X^1$ is hydrogen or halo.

The present invention resulted from the fact that N-cyclohexyl-3-mercaptopropionamide could not be prepared by presently employed procedures for preparing commercial biocides.

The preparation of two commercial isothiazolone biocides procedes through an appropriately substituted mercaptopropionamides. However, all attempts to use a similar procedure to prepare a cycloalkyl substituted mercaptopropionamide were unsuccessful.

The procesure has the following advantages:
Low raw material cost;
Low operating cost;
An all liquid process; and
Nitrosoamine precursor free.

The key to the process is in cofeeding sulfuric acid and a premixed acrylonitrile/alcohol.

DETAILED DESCRIPTION

The first two steps, which are the center of this invention, are described here.

STEP 1

Acrylamide

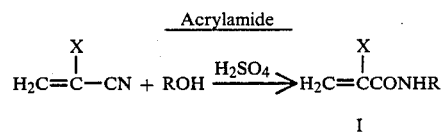

wherein X and R are as defined above.

Nitriles that are suitable for this preparation are those wherein X is hydrogen, alkyl(acylcic or cyclic) such as methyl, ethyl, propyl, butyl, pentyl, cyclopentyl, cyclohexyl and the like, or unsubstituted or substituted aryl for example phenyl or phenyl substituted with one or more dialkyl, halo, nitro, alkoxycarbonyl, alkoxy and the like, and R is secondary or tertiary alkyl such as isopropyl, cyclopentyl, cyclohexyl, tert-butyl, 2-methyl-2-butyl, or substituted or unsubstituted benzyl wherein the substitutent is one or more alkyl, halo, nitro, alkoxycarbonyl, alkoxy and the like. (Any olefins corresponding to dehydration of ROH, for example the dehydration of cyclohexanol to form cyclohexene or otherwise able to form a stable carbonium ion may also be used.) Inorganic acids which may be employed include sulfuric, p-toluic, hydrochloric, phosphic and the like. Sulfuric acid is the preferred inorganic acid. The acid which may be used should have a concentration in the range of from 50 to 100% and, preferably in the range of from about 96 to about 99.5%. The reaction can be carried out neat or in a solvent such as inert organic solvents including halobenzene and the like, or glacial acetic acid or primary alcohols such as methanol, ethanol and the like.

Preferably, a premixed solution of nitrile and alcohol (or olefin) and concentration sulfuric acid are added concurrently to a heel of solvent or sulfuric acid at temperature ranging from about 0° to about 65° C. The mole ratio of nitril to alcohol is in the range of from about 0.8 to about 1.2 and preferably 1.0. The mole ratio of sulfuric acid to nitrile (or alcohol) is in the range of from about 1.5 to about 3.0 and, preferably, 2.0. The temperature at which the reactants are mixed is dependent on the substrate nature, and is preferably above the freezing point of the reaction mixture and below the boiling point of the lowest boiling component. The whole mixture is then held at room temperature or some elevated temperature for from 1 to 24 hours. The organic solvent used for the entire process is then added to the above mixture followed by slow addition of water to produce the desired amide in the organic solvent. This mixture is ready for the second step (thiolation) without any further isolation or purification.

The only detected by-products from this procedure are hydrolyzed forms of the nitrile such as the amide and acid in about 0.2% weight of the total product mixture. Their existence at such small levels has not interfered with the thiolation step.

STEP 2

Thiolation if Acrylamide

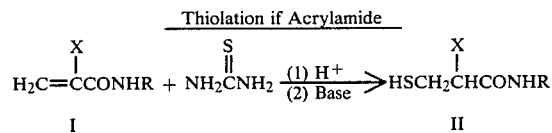

I                 II

The acrylamide, (I) produced in the previous step is directly treated with a thiolating agent selected from thiourea, carbon disulfide/sodium sulfide, hydrogen sulfide and the like in the same pot and the mixture is allowed to react at a temperature in the range of from about 0° to about 70° C. for about 30 minutes to about 3 hours. The mole ratio of thiourea to the starting alcohol or nitrile is generally in the range of from about 0.9 to about 1.2 and, is preferably 1.05. The thiolation is catalyzed by a strong acid such as hydrochloric, sulfuric, perchloric, p-toluenesulfonic acids and the like. Hydrochloric and sulfuric acids are preferable because they are cheaper and afford better yields. The above mixture is then treated with enough base to completely neutralize the mixture at a temperature in the range of from about 0° to about 70° C. for from 30 minutes to 3 hours. (Excess base should be avoided as it destroys the mercaptoamide.) Bases that can be employed includes sodium hydroxide, ammonium hydroxide, sodium carbonate, sodium bicarbonate, alkaline earth oxides, ammonia and the like. Hydrolysis with base can be done at lower temperature and brought to higher temperaturer for hold. Or it can be done and held at certain chosen temperature. After hydrolysis, the mercaptoamide solution in the specified organic solvent is dried, preferably by azeotropic removal of water employing those solvents which can form azeotropes with water for example chloroform, heptane, toluene and the like. Drying of the mercaptoamide solution is necessary as a small quantity of water can substantially lower the yield of the subsequent halogenation reaction. Other thiolating agents such as sodium sulfide, sodium hydrosulfide with combination of carbon disulfide are suitable for thiolating acrylamide (I). Typically, carbon disulfide is added to a solution of sodium sulfide at a molar ratio of 1.5 to 1.0 in methanol and water at temperatures ranging from 0° C. to 30° C. Acrylamide or its solution in an inert solvent as defined earlier is added to the above mixture at 20°-50° C. The resulting mixture is then hydrolyzed with mineral acid preferably hydrochloric or sulfuric acid. Upon layer separation and solvent removal, the mercaptoamide obtained is thus formulated into an appropriate solvent for the subsequent chlorination. The halogenation reaction has been previously described in U.S. Pat. No. 4,105,431 which is hereby incorporated by reference.

The following examples illustrate this invention; however, it is to be understood that the invention is not limited to the specific examples but is as described by the specification and appended claims.

EXAMPLE 1

N-Cyclohexyl-3-mercaptopropionamide

Step A—N-Cyclohexylacrylamide

Sulfuric acid (46.0 g) was placed in a 3-liter 3-neck flask and heated to 45° C. A mixture of acrylonitrile (94.5g) and cyclohexanol (180.2g) was prepared and added to the flask simultaneously with additional sulfuric acid (95.8%, 322.3 g) keeping the temperature at 45°-55° C. At the end of the addition, the brown solution was heated to 60° C. for 3 hours. The mixture was then poured into 3 liters of ice water with constant stirring. The white precipitate formed was filtered, washed with water until filtrate is no longer acidic and dried in a vacuum oven at 55° C. to yield N-cyclohexylacrylamide (242.4 g, 88%); m.p. 109°-110° C.

Step B—N-Cyclohexyl-3-mercaptopropionamide

A mixture of N-cyclohexylacrylamide (15.3 g), concentrated hydrochloric acid (19.4 g, 37.6%), thiourea (7.6 g) and water (10 g) was heated to 60° C. for 2 hours, cooled to 20° C. and sodium hydroxide (50%, 16 g) was slowly added under nitrogen keeping the temperature below 30° C. The resulting mixture was heated to 60° C. for 1 hour and extracted with methylene chloride (2×50 ml). Removal of the solvent afforded N-cyclohexyl-3-mercaptopropionamide (16.9 g) which was purified by vacuum distillation at 0.05 mm and 130° C. to yield 13.7 g of N-cyclohexyl-3-mercaptopropionamide; m.p. 73.5°-75.5° C.

EXAMPLE 2

N-Cyclohexyl-3-mercaptopropionamide

A pre-mix of acrylonitrile/cyclohexanol (13.3 g/25.1 g) and concentrated sulfuric acid (51.1 g) were added through two addition funnels into a flask containing chlorobenzene (60 g) at 45°-55° C. The mixture was then heated to 60°-70° C. for 3-5 hours and cooled to 20° C. when water (150 g) was added slowly. After 30 minutes stirring, thiourea (19 g) was added and the mixture brought to 60° C. for 1 hour. On cooling to 20° C., caustic (50%, 80 g) was added between 20b 60° C. C under nitrogen and held at 60° C. for 1 hour. The organic layer was separated and washed with warm water to yield 33.9 of N-cyclohexyl-3-mercaptopropionamide in chlorobenzene (72.4% yield).

EXAMPLE 3

(N-Cyclohexyl-3-mercatopropionamide

Carbon disulfide (76 g) was added to a mixture of sodium sulfide (55 g) in methanol (80 g) and water (80 g) and kept at 20° C. To this was slowly added N-cyclohexylacrylamide (100 g) maintaining the pot temperature at 20°-30° C. The resulting solution was stirred for an additional 2-3 hour and neutralized with concentrated hydrochloric acid. The organic layer was separated, washed with water and evaporated to dryness to afford 122.6 g of N-cyclohexyl-3-mercaptopropionamide (90.5% yield).

PREPARATION OF OTHER AMIDES

EXAMPLE 4

N-Tert-butylacrylamide

To a solution of acrylonitrile (5.3 g), tert-butyl alcohol (7.4 g) and acetic acid (50 ml), cooled in an ice-bath, was added dropwise concentrated sulfuric acid (10.1 g, 97%) at a temperature below 40° C. The mixture was held at 40° C. for 1 hour and then poured into 200 g of ice water with constant stirring. The precipitate was filtered, washed with water and dried to afford N-tert-butylacrylamide (10.3 g, 82.4%); m.p. 124°–6° C.

EXAMPLE 5

N-(2-Methyl-2-butyl)methacrylamide

2-Methyl-2-butene (7.0 g) was added to a stirred mixture of methacrylonitrile (6.7 g) in acetic acid (50 ml) and concentrated sulfuric acid (10 g) at 10° to 20° C. The mixture was allowed to stand overnight at room temperature, and then poured into 200 g of water and extracted with methylene chloride (2×100 ml). The methylene chloride solution was dried over sodium sulfate, the solid filtered off and the methylene chloride evaporated to afford an oily product. Distillation of the product at 10 mm yielded N-(2-methyl-2-butyl)methacrylamide (10.1 g, 65%); bp 84° C.

PREPARATION OF ISOTHIAZOLES

EXAMPLE 6 4,5

Dichloro-N-cyclohexylisothiazolone

A 45% solution (100 g) of N-cyclohexyl-3-mercaptopropionamide in chlorobenzene was fed into a reactor containing a small heel of the same solvent concurrently with chlorine. (The molar feed ratio of chlorine to propionamide ranges from 3.0 to 3.6.) The temperature was kept at 40°–70° C. during the chlorination. After the end of propionamide fed, the remaining chlorine to make up to 4.0 equivalents was charged at the same temperature. The mixture was held for 30 minutes, washed with water, 80 to 85% solvent of the solvent removed and the crude material was recrystallized from acetone/water to afford 36.0 of white crystals of 4,5-dichloro-N-cyclohexylisothiazolone (59.5% yield); m.p. 115°–116° C.

What is claimed is:

1. A process for preparing a compound of the formula:

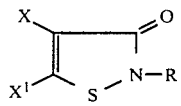

wherein $X^1$ is hydrogen or halo:
X is hydrogen, $C_1$–$C_5$alkyl, $C_2$–$C_6$alkenyl, phenyl or phenyl $C_1$–$C_5$alkyl and
R is an isopropyl, cyclopentyl, cyclohexyl, tert-butyl, 2-methyl-2-butyl, benzyl or substituted benzyl wherein the substituent is one or more $C_1$–$C_5$alkyl, halo, or nitro, which consisting essentially in cofeeding a mixture of an unsaturated nitrile of the formula:

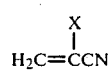

wherein X is as defined above and an alcohol of the formula ROH with sulfuric acid having a concentration of from about 96 to about 99.5% at a temperature in the range of from about 0° to about 65° C. wherein the mole ratio of nitrile to alcohol is in the range of from about 0.7 to about 1.2 and the mole ratio of sulfuric acid to nitrile is in the range of from about 1.5 to about 3.0 followed by the slow addition of water to form a propionamide of the formula:

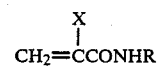

wherein X is as defined above, followed by treatment with a thiolating agent selected from thiourea, carbon disulfide/sodium sulfide or hydrogen sulfide at a temperature in the range of from about 0° C. to about 70° C. wherein the mole ratio of thiolating agent to the starting nitrile is in the range of from about 0.9 to about 1.2 to afford an N-substituted-3-mercaptopropionamide of the formula:

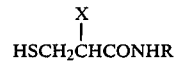

wherein X as defined above followed by halogenation to afford the desired compound.

2. The process of claim 1 wherein the alcohol is selected from tert-butyl alcohol, iso-propyl alcohol, benzyl alcohol, or cyclohexanol.

3. A process for preparing a compound of the formula:

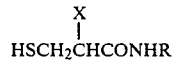

wherein
X is hydrogen, $C_1$–$C_5$alkyl, $C_2$–$C_6$alkenyl, phenyl or phenyl $C_1$–$C_5$alkyl and
R is an isopropyl, cyclopentyl, cyclohexyl, tert-butyl, 2-methyl-2-butyl, benzyl or substituted benzyl wherein the substituent is one or more $C_1$–$C_5$alkyl, halo, or nitro, which consists essentially in cofeeding a mixture of a compound of the formula:

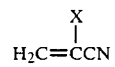

wherein X is as defined above and an alcohol of the formula ROH with sulfuric acid having a concentration of from about 96 to about 99.5% at a temperature in the range of from about 0° to about 65° C. wherein the mole ratio of nitrile to alcohol is in the range of from about 0.8 to about 1.2 and the mole ratio of sulfuric acid to nitrile is in the range of from about 1.5 to about 3.0 followed by the slow addition of water to form a propionamide of the formula:

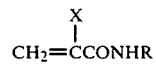

wherein X is as defined above, followed by treatment with a thiolating agent selected from thiourea, carbon disulfide/sodium sulfide or hydrogen sulfide at a temperature in the range of from about 0° C. to about 70° C. wherein the mole ratio of thiolating agent to the starting nitrile is in the range of from about 0.9 to about 1.2.

4. The process of claim 3 wherein the alcohol is selected from tert-butyl alcohol, iso-propyl alcohol, benzyl alcohol, or cyclohexanol.

5. A process for preparing 4,5-dichloro-N-cyclohexyl isothiazolone which consists essentially in cofeeding a mixture of acrylonitrile and cyclohexanole with sulfuric acid having a concentration of from about 96 to about 99.5% at a temperature in the range of from about 0° to about 65° C. wherein the mole ratio of nitrile to alcohol is in the range of from about 0.8 to about 1.2 and the mole ratio of sulfuric acid to nitrile is in the range of from about 1.5 to about 3.0 followed by the slow addition of water to form N-cyclohexylacrylamide, followed by treatment with a thiolating agent selected from thiourea, carbon disulfide/sodium sulfide or hydrogen sulfide at a temperature in the range of from about 0° C. to about 70° C. wherein the mole ratio of thiolating agent to the starting nitrile is in the range of from about 0.9 to about 1.2 to afford N-cyclohexyl-3-mercaptopropionamide followed by halogenation to afford the compound.

* * * * *

UNITED STATES PATENT AND TRADEMARK OFFICE
CERTIFICATE OF CORRECTION

PATENT NO. : 4,868,310
DATED : September 19, 1989
INVENTOR(S) : Sou-Jeng Chang

It is certified that error appears in the above-identified patent and that said Letters Patent is hereby corrected as shown below:

Column 1, line 52, "mwherein" should read --wherein--.

Column 2, line 4, "procesure" should read --procedure--.

Column 5, lines 22 & 23 should read

--Example 6
4,5-Dichloro-N-cyclohexylisothiazolone--.

Column 5, line 67, claim 1, "0.7" should read --0.8--.

Signed and Sealed this

Twenty-eighth Day of August, 1990

Attest:

HARRY F. MANBECK, JR.

*Attesting Officer*   *Commissioner of Patents and Trademarks*